United States Patent [19]
Goto et al.

[11] 4,060,559
[45] Nov. 29, 1977

[54] PROCESS FOR PREPARING O-PHENYLPHENOL

[75] Inventors: Hideo Goto; Nobuyori Shibamoto; Shunsaku Tanaka, all of Wakayama, Japan

[73] Assignee: Sugai Chemical Industry Co., Ltd., Wakayama, Japan

[21] Appl. No.: 682,524

[22] Filed: May 3, 1976

[30] Foreign Application Priority Data

May 14, 1975 Japan .................................. 50-57806
May 12, 1975 Japan .................................. 50-56272

[51] Int. Cl.² ............................................ C07C 37/06
[52] U.S. Cl. .................................. 260/620; 252/439; 252/440
[58] Field of Search ................. 260/620; 252/439, 440

[56] References Cited

U.S. PATENT DOCUMENTS

| | | | |
|---|---|---|---|
| 3,580,970 | 5/1971 | Swift ..................................... | 260/620 |
| 3,923,695 | 12/1975 | Nussel et al. .......................... | 260/620 |
| 3,972,951 | 8/1976 | Kapner et al. ........................ | 260/620 |
| 3,980,716 | 9/1976 | Elliot .................................... | 260/620 |

FOREIGN PATENT DOCUMENTS

1,543,878  1/1970  Germany ............................. 260/620

*Primary Examiner*—Norman Morgenstern
*Attorney, Agent, or Firm*—Larson, Taylor and Hinds

[57] ABSTRACT

A process for preparing o-phenylphenol by dehydrogenating at least one of cyclohexanone dimer and o-cyclohexylphenol in the presence of a catalyst, characterized in that the catalyst comprises a metal oxide carrier, and at least one of alkali metal salts of sulfur-oxygen acids and at least one of platinum and palladium supported by the carrier.

7 Claims, No Drawings

PROCESS FOR PREPARING O-PHENYLPHENOL

This invention relates to a process for preparing o-phenylphenol, and more particularly to a process for preparing o-phenylphenol by dehydrogenating cyclohexanone dimer or o-cyclohexylphenol.

o-Phenylphenol was produced chiefly as a by-product of the alkali hydrolysis of chlorobenzene for the synthesis of phenol. With the process of petrochemistry, however, the cumene process has taken over the above-mentioned process, consequently reducing the supply of o-phenylphenol as the by-product despite the increasing demand for the compound for use in surfactants and disinfectants and giving rise to the necessity to develop a process for the production of o-phenylphenol per se in order to compensate for the reduction in the supply of the by-product. Accordingly processes for producing o-phenylphenol have been developed in which cyclohexanone dimer or o-cyclohexylphenol is catalytically dehydrogenated. They are grouped into three types. Publicly Disclosed Japanese Patent Publication No. 11823/1972 discloses one type of the processes which uses a catalyst containing copper, nickel, aluminum and chromium and at least one of alkali sulfates and alkali carbonates. The process of another type which is disclosed in Publicly Disclosed Japanese Patent Publication No. 35365/1974 uses a catalyst comprising a carrier such as alumina or activated carbon having a relatively large surface area and a small amount of palladium or platinum adsorbed by the carrier. Publicly Disclosed Japanese Patent Publication No. 72240/1974 discloses a process of the third type which uses a catalyst comprising an alumina or silica-alumina carrier and specified amounts of platinum and a hydroxide, oxide or carbonate of sodium or potassium. However, these processes have the following drawbacks. The first-mentioned process is industrially very disadvantageous in that it requires evaporation and purification steps because of the low selectivity in giving o-phenylphenol. When palladium is used in the process of the second type, problems are encountered in the thermal stability and toxicity of the catalyst and it is extremely difficult to maintain a high selectivity for a prolonged period of time. Furthermore when platinum is used in this process, the life of the catalyst is relatively short while the selectivity for o-phenylphenol is not fully satisfactory. Being more excellent in the life of the catalyst than the process using platinum and/or palladium, the process of the third type is not sufficient and likely to give dibenzofuran, biphenyl or like by-product.

An object of this invention is to provide a process for preparing o-phenylphenol with a high selectivity.

Another object of this invention is to provide a process for preparing o-phenylphenol with a catalyst which is serviceable for a prolonged period of time, or in other words, to provide a catalyst having a prolonged life for use in the production of o-phenylphenol.

Still another object of this invention is to provide a process for preparing o-phenylphenol with the formation of by-product greatly reduced.

These and other objects of this invention will become apparent from the following description.

In preparing o-phenylphenol by dehydrogenating at least one of cyclohexanone dimer and o-cyclohexylphenol in the presence of a catalyst, the objects of this invention can be fulfilled by the use of a catalyst comprising a metal oxide carrier, and at least one of alkali metal salts of sulfur-oxygen acids and at least one of platinum and palladium which are supported by the carrier.

In preparing o-phenylphenol by dehydrogenating at least one of cyclohexanone dimer and o-cyclohexylphenol, our research has revealed that when the dehydrogenation is conducted in the presence of a catalyst comprising a metal oxide carrier, and platinum and/or palladium and an alkali metal salt of sulfur-oxygen acid supported by the carrier, the catalyst exhibits a higher selectivity with a longer service life than the catalysts described above while greatly reducing the formation of by-product. Based on this finding, the invention has been accomplished.

The catalysts to be used in this invention are novel catalysts which have not been used for the production of o-phenylphenol. The catalysts are composed of a metal oxide carrier, and platinum and/or palladium and at least one of alkali metal salts of sulfur-oxygen acids which are supported by the carrier. The useful metal oxide carriers include those heretofore used such as silica, alumina, magnesia, calcium oxide, etc. Preferable examples are alumina, silica, alumina-silica, alumina-magnesia and alumina-calcium oxide, and $\gamma$-alumina is especially preferable. The specific surface area of the metal oxide carrier to be used is usually 100 to 300 $m^2/g$, preferably about 150 to 250 $m^2/g$ (as determined by BET method). The carrier may have any of suitable forms such as pellets, particles, granules, etc.

The platinum and/or palladium may be so supported by the carrier that they act as such elements when used substantially in the form of a catalyst. The amount of platinum and/or palladium to be used is 0.1 to 3.0% by weight, preferably about 0.3 to about 1.0% by weight, based on the carrier. With extremely lesser amounts, low catalytic activity results, whereas amounts above 3.0% by weight will not give improved results.

The alkali metal salts of sulfur-oxygen acids useful in this invention are versatile; examples are alkali metal salts and alkali metal hydrogen salts of sulfuric acid, sulfurous acid and thiosulfuric acid. More specific examples are sodium sulfate, potassium sulfate, rubidium sulfate, cesium sulfate and like alkali sulfates; sodium thiosulfate, potassium thiosulfate and like alkali thiosulfates; sodium sulfite, potassium sulfite and like alkali sulfites; sodium bisulfate, potassium bisulfate and like alkali bisulfates; and sodium bisulfite, potassium bisulfite and like alkali bisulfites. Preferable among these examples are sodium sulfate, potassium sulfate, rubidium sulfate, cesium sulfate, sodium thiosulfate, sodium bisulfite, potassium bisulfite, potassium thiosulfate, etc. The amount of the sulfur-oxygen acid salt to be supported by the carrier is about 0.1 to about 10% by weight, preferably about 2.0 to about 5.0% by weight, based on the carrier. If the amount of sulfur-oxygen acid salt supported by the carrier is less than 0.1% by weight, an increased amount of by-product will be formed, whereas above 10% by weight, reduced catalytic activity tends to result.

According to this invention, the metal oxide carrier may be made to support platinum and/or palladium and the sulfur-oxygen acid salt by any method, insofar as the desired amounts of the effective components can be supported by the carrier. Either the sulfur-oxygen acid salt, or platinum and/or palladium may be supported first, or both may be supported at the same time. Preferably, however, platinum and/or palladium may be supported first, and then the sulfur-oxygen acid salt. Typically platinum and/or palladium can be supported by the carrier by the steps of immersing the metal oxide carrier of a suitable form in an aqueous solution of platinum compound such as platinum chloride and/or palladium compound such as palladium chloride, drying the carrier, heating the carrier in an atmosphere at about 300° to about 400° C and thereafter reducing the product with hydrogen at a temperature of about 300° to about 400° C. Further the sulfur-oxygen acid salt can be supported by the carrier typically for example by the steps of immersing the suitably shaped metal oxide carrier in an aqueous solution of the salt, drying the carrier and then baking the product at about 300° to about 400° C. The metal oxide carrier can be made to support the sulfur-oxygen acid salt and platinum and/or palladium at the same time, for example, by immersing the carrier in an aqueous solution of the salt and platinum compound and/or palladium compound, drying the carrier, then heating the same in an inert gas at 300° to 400° C and reducing the heated product with hydrogen at the same temperature.

The novel catalyst of the present invention may further support at least one of alkali metal oxides. The use of these oxides give the novel catalyst a slightly prolonged life. The alkali metal oxides to be supported in the present invention are, for example, sodium oxide, potassium oxide, cesium oxide, etc.

In the present invention the alkali metal oxide may be supported by any method. Typically the alkali metal oxide can be supported on the carrier by the steps of immersing the carrier in an aqueous solution of alkali metal compound and heating the carrier at 300° to 400° C. The alkali compounds to be used are versatile; examples are alkali metal oxide, alkali metal hydroxide and alkali metal carbonate. Preferable among these examples are sodium hydroxide, sodium carbonate, potassium hydroxide, potassium carbonate, etc. The amount of the compound is up to about 8.0% by weight, preferably about 1.0 to about 7.0% by weight, in terms of alkali metal oxide based on the carrier.

When dehydrogenating at least one of cyclohexanone dimer and o-cyclohexylphenol with the novel catalyst described, either a vapor-phase method or a liquid-phase method can be adopted. However, the vapor-phase method is preferable in view of the ease of reaction procedure and reaction efficiency. The vapor-phase reaction can be effected, for example, by vaporizing the dimer of cyclohexanone and/or o-cyclohexylphenol as by a pre-heater and feeding the resulting vapor, as it is or as diluted with an inert gas, to a reactor packed with the catalyst. The feed rate of the starting material may be suitably determined in accordance with the reaction temperature and the kind of the catalyst. Material calculated as a liquid at room temperature is fed at a rate of usually 0.1 to 1.5 times, preferably 0.2 to 0.7 time, the volume of the catalyst per hour.

The reaction temperature also varies with the kind of the catalyst and the feed rate of the material and is usually about 250° to about 420° C, preferably about 300° to about 400° C.

The catalysts of this invention can be regenerated effectively by usual methods, for example, by oxidizing the catalyst with air or a mixture of air and nitrogen gas at about 300° to about b 400° C and thereafter reducing the catalyst with hydrogen at about 300° to about 350° C. The catalyst thus regenerated is almost as active as a fresh catalyst.

EXAMPLE 1

γ-Alumina pellets (75 g) having a specific surface area of 190 to 230 m²/g, diameter of 2.9 mm and thickness of 3.0 mm are immersed in 200 g of aqueous solution containing 1 g of chloroplatinic acid hexahydrate for full impregnation and are thereafter withdrawn and dried. The pellets are placed in a tube and heated in a nitrogen atmosphere at 350° C for 3 hours. Subsequently the pellets are reduced at the same temperature for 3 hours with hydrogen introduced into the tube to cause the pellets to support platinum. 50 g of the resulting mass is immersed in 60 g of aqueous solution containing 2.5 g of potassium sulfate and, after having been fully impregnated with the solution, the mass is withdrawn, dried and then heated at 250° C for 3 hours to obtain a catalyst of this invention.

A 34.5 ml quantity of the catalyst is packed in a heat-resistant glass reaction tube, 27 mm in inside diameter and 1,000 mm in length. Cyclohexanone dimer is fed to the tube at a rate of 15.5 ml/hr. while introducing hydrogen into the tube at a rate of 290 ml/min. and maintaining the reaction temperature at 300° to 400° C. During the reaction, the resulting product is sampled from time to time and analyzed by gas chromatography. It is found that the conversion of the cyclohexanone dimer starting material achieved is always 100% over the reaction period of 2,000 hours. The selectivity for o-phenylphenol is also measured with the result given in Table 1 below.

EXAMPLE 2 to 7

The same procedure as in Example 1 is repeated except that in place of potassium sulfate, sodium sulfate, rubidium sulfate, cesium sulfate, sodium thiosulfate, sodium bisulfite and a mixture of sodium sulfate and rubidium sulfate (3:2 in weight ratio) are used in the Examples respectively. The same analysis as conducted in Example 1 confirms 100% conversion in each Example. Table 1 also shows the selectivities for o-phenylphenol.

EXAMPLE 8

The same procedure as in Example 1 is repeated except that o-cyclohexylphenol is used in place of the cyclohexanone dimer. The conversion is found to be always 100% over the reaction period of 2,000 hours. The selectivity of o-phenylphenol measured is given in Table 1.

EXAMPLE 9 the same procedure as in Example 1 is repeated except that pellets of a mixture of γ-alumina and magnesia (90:10 in weight ratio, baked product at 1000° C for 3 hours) are used in place of the γ-alumina pellets. The conversion is found to be always 100% over the reaction period of 2,000 hours. Table 1 gives the selectivity for o-phenylphenol measured.

EXAMPLE 10

The same procedure as in Example 1 is repeated except that pellets of γ-alumina-calcium oxide (85:15 in weight ratio, baked product at 600° C for 3 hours) are used in place of the γ-alumina pellets. The conversion of the cyclohexanone dimer is confirmed to be always 100% during the 2,000 hours' reaction. Table 1 gives the selectivity for o-phenylphenol measured.

EXAMPLE 11

The same procedure as in Example 1 is repeated except that pellets of alumina-silica (90:10 in weight ratio, baked product at 800° C for 3 hours) are used in place of the γ-alumina pellets. The conversion of the cyclohexanone dimer is found to be always 100% during the reaction period of 2,000 hours. The selectivity is given in Table 1.

The alkali metal salts of sulfur-oxygen acids used in Examples 2 to 7 are as follows:
Example 2: sodium sulfate.
Example 3: rubidium sulfate.
Example 4: cesium sulfate.
Example 5: mixture of sodium sulfate and rubidium sulfate (3:2 in weight ratio).
Example 6: sodium thiosulfate.
Example 7: sodium bisulfite.

Table 1

| Reaction period (hr.) | Selectivity for o-phenylphenol (mol %) Example | | | | | | | | | | | Comp. Ex-ample |
|---|---|---|---|---|---|---|---|---|---|---|---|---|
| | 1 | 2 | 3 | 4 | 5 | 6 | 7 | 8 | 9 | 10 | 11 | |
| 2 | — | 88.7 | — | — | — | — | — | — | — | 89.2 | 94.0 | — |
| 3 | 94.1 | — | — | — | — | — | 82.0 | 96.0 | — | — | — | 62.0 |
| 4 | — | — | 86.7 | 83.3 | 88.0 | — | — | — | 86.2 | — | — | — |
| 5 | — | — | — | — | — | 92.7 | — | — | — | — | — | 63.0 |
| 6 | 94.2 | 90.7 | 86.3 | 82.9 | 90.2 | — | 85.1 | 96.1 | 90.5 | 91.3 | 94.3 | — |
| 8 | — | — | — | — | — | — | 89.0 | — | — | — | — | — |
| 9 | 94.4 | — | 90.4 | — | — | — | — | 96.2 | — | — | — | — |
| 10 | — | — | — | — | — | 93.0 | — | — | — | — | 94.4 | — |
| 11 | — | 90.8 | — | 87.1 | — | — | — | — | — | 92.0 | — | — |
| 12 | 94.4 | — | 91.3 | — | 91.0 | — | 90.2 | 96.2 | 93.0 | — | 94.4 | — |
| 20 | — | — | — | — | — | — | — | — | 95.0 | — | — | 63.8 |
| 50 | — | — | — | — | — | 92.8 | 91.0 | — | — | — | — | 64.1 |
| 100 | 94.0 | 90.0 | 91.5 | 92.0 | 92.5 | — | 91.3 | 96.0 | 94.6 | 91.0 | 93.9 | — |
| 500 | 93.5 | 89.6 | 91.0 | 91.0 | 92.0 | 92.0 | 90.0 | 94.3 | 94.2 | 90.4 | 93.5 | — |
| 1200 | 92.0 | 89.0 | 90.4 | 90.1 | 91.3 | 91.2 | 89.0 | 94.0 | 93.8 | 90.0 | 92.3 | — |
| 2000 | 91.8 | 88.0 | 90.0 | 89.0 | 90.1 | 90.1 | — | — | 92.0 | 89.2 | 92.0 | — |

EXAMPLE 12

γ-Alumina pellets (75 g) having a specific surface area of 190 to 230 m²/g, diameter of 2.9 mm and thickness of 3.0 mm are immersed in an aqueous solution containing 1g of chloroplatinic acid hexahydrate for full impregnation and are thereafter withdrawn and dried. The pellets placed in a tube and heated in a nitrogen atmosphere at 350° C for 3 hours. Subsequently the pellets are reduced at the same temperature for 3 hours with hydrogen introduced into the tube to cause the pellets to support platinum. 50g of the resulting mass is immersed in 60 g of aqueous solution containing 1g of potassium hydroxide and, after having been fully impregnated with the solution, the mass is withdrawn, dried and then heated at 350° C for 3 hours. The resulting pellet is further fully immersed in a solution of 1.5g of sodium thiosulfate pentahydrate and 60 ml of deionized water, then withdrawn and heated at 350° C for 3 hours to obtain a catalyst of the invention.

A 34.5 ml quantity of the catalyst is packed in a heat-resistant glass reaction tube, 27 mm in inside diameter and 1,000 mm in length. Cyclohexanone dimer is fed to the tube at a rate of 15.5 ml/hr. while introducing hydrogen into the tube at a rate of b 290 ml/min. and maintaining the reaction temperature at 300° – 400° C.

During the reaction, the resulting product is sampled from time to time and analyzed by gas chromotagrophy. It is found that the conversion of the cyclohexanone dimer starting materials achieved is always 100% over the reaction period of 2,000 hours. The selectivity for o-phenylphenol is also measured with the result given in Table 2 below.

EXAMPLE 13

The same procedure as in Example 12 is repeated except that pellets of a mixture of γ-alumina and magnesia (90:10 in weight ratio, baked product at 1000° C for 3 hours) are used in place of the γ-alumina pellets. The conversion found to be always 100% over the reaction period of 2,000 hours. Table 2 gives the selectivity for o-phenylphenol measured.

EXAMPLE 14

The same procedure as in Example 1 is repeated except that in place of 1g of chloroplatinic acid hexahydrate, 2.5g of potassium sulfate and at a rate of 15.5 ml/hr. of cyclohexanone dimer, 1.25g of chloropalladium, 2.0g of potassium sulfate and at a rate of 8.0 ml/hr. are employed. The conversion is found to be always 100% over the reaction period of 2,000 hours. Table 2 gives the selectivity for o-phenylphenol measured.

EXAMPLE 15

The same procecure as in Example 1 is repeated except that in place of 1g of chloroplatinic acid hexahydrate, 1g of a mixture of chloroplatinic acid hexahydrate and chloropalladium (90:10 in weight ratio) is used. The conversion is found to be always 100% over the reaction period of 2,000 hours. Table 2 gives the selectivity for o-phenylphenol measured.

Table 2

| Reaction period (hr.) | Selectivity for o-phenylphenol (mol %) Example | | | |
|---|---|---|---|---|
| | 12 | 13 | 14 | 15 |
| 1 | — | — | 87.2 | — |
| 2 | — | — | — | — |
| 3 | — | — | 90.1 | 91.1 |
| 4 | — | 86.2 | — | — |
| 5 | 93.7 | — | 91.7 | — |
| 6 | — | 90.5 | — | — |
| 7 | — | — | — | — |
| 8 | — | — | — | — |
| 9 | — | — | — | — |
| 10 | 94.4 | — | 92.0 | 91.4 |
| 11 | — | — | — | — |
| 12 | — | 93.0 | — | — |
| 20 | — | 95.0 | 91.1 | — |
| 50 | 92.8 | — | 90.8 | 91.3 |
| 100 | 92.8 | 94.6 | 90.0 | 91.0 |
| 500 | 92.3 | 94.2 | 87.4 | 90.2 |
| 1200 | 91.5 | 93.8 | — | 89.8 |

Table 2-continued

| Reaction period (hr.) | Selectivity for o-phenylphenol (mol %) Example | | | |
|---|---|---|---|---|
| | 12 | 13 | 14 | 15 |
| 2000 | 90.4 | 92.0 | — | — |

What we claim is:

1. A process for preparing o-phenylphenol by dehydrogenating at least one of cyclohexanone dimer and o-cyclohexylphenol in the presence of a catalyst, characterized in that the catalyst consists essentially of a metal oxide carrier, and about 0.1 to about 10% by weight based on the carrier of at least one of alkali metal salts of sulfur-oxygen acids and 0.1 to 3.0% by weight based on the carrier of at least one of platinum and palladium supported by the carrier.

2. The process for preparing o-phenylphenol according to claim 1 in which said alkali metal salt of sulfur-oxygen acid is at least one of alkali metal salts and alkali metal hydrogen salts of sulfuric acid, sulfurous acid and thiosulfuric acid.

3. The process for preparing o-phenylphenol according to claim 2 in which said alkali metal salt of sulfur-oxygen acid is at least one of sodium sulfate, potassium sulfate, rubidium sulfate, cesium sulfate, sodium thiosulfate, sodium bisulfite, potassium bisulfite and potassium thiosulfate.

4. The process for preparing o-phenylphenol according to claim 1, in which said metal oxide carrier is at least one of silica, alumina, magnesia and calcium oxide carrier.

5. The process for preparing o-phenylphenol according to claim 4, in which said metal oxide carrier is alumina, silica, alumina-calcium oxide, alumina-silica or alumina-magnesia carrier.

6. The process for preparing o-phenylphenol according to claim 5, in which said metal oxide is γ-alumina.

7. The process for preparing o-phenylphenol according to claim 1 in which at least one of said alkali metal salts of sulfur oxygen acids is supported by the carrier in an amount of about 2.0 to about 5.0% by weight based on the carrier.

* * * * *